United States Patent
Griswold et al.

(10) Patent No.: US 9,536,423 B2
(45) Date of Patent: Jan. 3, 2017

(54) FIBER OPTIC TELEMETRY FOR SWITCHED-MODE CURRENT-SOURCE AMPLIFIER IN MAGNETIC RESONANCE IMAGING (MRI)

(71) Applicant: Case Western Reserve University, Cleveland, OH (US)

(72) Inventors: Mark Griswold, Shaker Heights, OH (US); Michael Twieg, Cleveland, OH (US)

(73) Assignee: Case Western Reserve University, Cleveland, OH (US)

(*) Notice: Subject to any disclaimer, the term of this patent is extended or adjusted under 35 U.S.C. 154(b) by 552 days.

(21) Appl. No.: 14/053,305

(22) Filed: Oct. 14, 2013

(65) Prior Publication Data

US 2014/0292324 A1    Oct. 2, 2014

Related U.S. Application Data

(60) Provisional application No. 61/806,907, filed on Mar. 31, 2013.

(51) Int. Cl.

| | |
|---|---|
| *G01V 3/00* | (2006.01) |
| *G08C 23/06* | (2006.01) |
| *G01R 33/36* | (2006.01) |
| *G01R 33/56* | (2006.01) |
| *G01R 33/48* | (2006.01) |
| *G01R 33/58* | (2006.01) |

(Continued)

(52) U.S. Cl.
CPC ............. *G08C 23/06* (2013.01); *A61B 5/0017* (2013.01); *A61B 5/0073* (2013.01); *A61B 5/4244* (2013.01); *A61K 49/06* (2013.01); *G01R 33/3614* (2013.01); *G01R 33/3692* (2013.01); *G01R 33/4822* (2013.01); *G01R 33/56* (2013.01); *G01R 33/5608* (2013.01); *G01R 33/56366* (2013.01); *G01R 33/58* (2013.01); *A61B 5/055* (2013.01)

(58) Field of Classification Search
USPC .......................................................... 324/307
See application file for complete search history.

(56) References Cited

U.S. PATENT DOCUMENTS

| | | | |
|---|---|---|---|
| 4,949,040 A * | 8/1990 | Proksa ............... | G01R 33/3621 324/307 |
| 5,739,691 A * | 4/1998 | Hoenninger, III . | G01R 33/3621 324/307 |

(Continued)

*Primary Examiner* — Rodney Fuller
(74) *Attorney, Agent, or Firm* — Quarles & Brady LLP; Jack Cook

(57) ABSTRACT

Example systems, apparatus, circuits, and other embodiments described herein concern acquiring telemetry data from an MR system and providing the telemetry data via fiber optic cable. One example apparatus includes a telemetry signal acquisition element (e.g., circuit, circuit component) that is configured to acquire a telemetry signal from a component in the MR apparatus. The component may be, for example, a transmit coil or an on-coil amplifier. The example apparatus also includes a fiber optic cable that is configured to carry an output signal from the MR apparatus through a field produced by the MR apparatus. The example apparatus also includes a telemetry signal output element that is configured to produce the output signal from the telemetry signal and to transmit the output signal via the fiber optic cable.

22 Claims, 11 Drawing Sheets

(51) Int. Cl.
   *A61K 49/06*   (2006.01)
   *A61B 5/00*    (2006.01)
   *G01R 33/563*  (2006.01)
   *A61B 5/055*   (2006.01)

(56) References Cited

U.S. PATENT DOCUMENTS

| | | | | |
|---|---|---|---|---|
| 6,339,717 B1* | 1/2002 | Baumgartl | ............ | G01R 33/54 |
| | | | | 378/145 |
| 6,567,118 B1* | 5/2003 | Al-Araji | ................ | H04N 7/102 |
| | | | | 348/180 |
| 6,977,502 B1* | 12/2005 | Hertz | ................. | G01R 33/3621 |
| | | | | 324/318 |
| 7,378,844 B2* | 5/2008 | Watkins | ............... | G01R 33/283 |
| | | | | 324/304 |
| 7,888,934 B2* | 2/2011 | Fukuchi | ............. | G01R 33/3415 |
| | | | | 324/307 |
| 2010/0260293 A1* | 10/2010 | Roeven | ............. | G01R 33/3621 |
| | | | | 375/340 |
| 2012/0020259 A1* | 1/2012 | Bollenbeck | ............ | A61B 5/055 |
| | | | | 370/297 |
| 2012/0286787 A1* | 11/2012 | Van Liere | .......... | G01R 33/3692 |
| | | | | 324/322 |
| 2012/0319884 A1* | 12/2012 | Bollenbeck | ........ | G01R 33/3621 |
| | | | | 341/155 |
| 2013/0119982 A1* | 5/2013 | Pirkl | .................. | G01R 33/3621 |
| | | | | 324/309 |
| 2013/0241547 A1* | 9/2013 | Biber | ................. | G01R 33/3415 |
| | | | | 324/307 |
| 2014/0062480 A1* | 3/2014 | Bollenbeck | ........ | G01R 33/3621 |
| | | | | 324/309 |
| 2014/0125504 A1* | 5/2014 | Braswell | ............... | H03M 3/344 |
| | | | | 341/110 |
| 2015/0097711 A1* | 4/2015 | Schuurmans | ........... | H03M 3/39 |
| | | | | 341/143 |
| 2015/0109159 A1* | 4/2015 | Liu | ....................... | H03M 3/398 |
| | | | | 341/143 |
| 2015/0295587 A1* | 10/2015 | Garcia Gonzalez | .. | H03M 3/356 |
| | | | | 341/121 |

* cited by examiner

FIBER OPTIC TELEMETRY FOR SWITCHED-MODE CURRENT-SOURCE AMPLIFIER IN MAGNETIC RESONANCE IMAGING (MRI)

PRIORITY CLAIM

This application claims the benefit of U.S. Provisional Patent Application 61/806,907 titled "Medical Imaging", filed Mar. 31, 2013.

BACKGROUND

Magnetic resonance imaging (MRI), nuclear magnetic resonance (NMR), and other magnetic resonance (MR) systems continue to become more sophisticated, powerful, precise, and complicated. MR systems rely on transmit coils to expose volumes to precisely controlled radio frequency (RF) energy. These RF transmit coils have also continued to become more sophisticated, powerful, and complicated. One recent advance involves using on-coil switched-mode current-source amplifiers.

MR involves the transmission of RF energy. RF energy used to produce MR may be transmitted by a coil. Resulting MR signals may also be received by a coil. Precisely controlling the generation of RF energy used to produce MR is desired to improve the resulting MR signals. However, conditions may change during application of RF energy. For example, circuits involved in producing RF energy may over-perform, under-perform, or fail completely. Yet sophisticated integration between numerous co-operating components may be required to produce and maintain precise conditions employed for producing MR.

The field of coil design using on-coil switched-mode amplifiers for parallel transmission is relatively new. For example, U.S. Pat. No. 7,671,595, which issued on Mar. 2, 2010 to one of these same inventors, presented an early on-coil switched-mode amplifier. U.S. Pat. No. 7,671,595 (the '595 patent) is entitled "On-coil Switched-mode Amplifier for Parallel Transmission in MRI" and describes an on-coil current-mode class-D (CMCD) amplifier that may be used to produce MRI transmission-coil excitations at desired RF frequencies. The on-coil CMCD amplifier is capable of performing within or proximate to the bore of the MRI magnet or within less than one wavelength of the RF signal produced by the transmit coil or at other positions or locations. Providing an on-coil amplifier allows digital control signals to be sent to the coil assembly, improving synchronization between the transmission-coils while reducing interference, cross talk, physical space requirements associated with cables, and heating normally associated with parallel transmission MRI systems.

Once this type of coil had been built, additional research using the new on-coil switched-mode amplifier revealed the need for further refinements including those presented in U.S. Pat. No. 8,294,464, which issued on Oct. 23, 2012 to one of these same inventors and in U.S. Pat. No. 8,294,465, which also issued on Oct. 23, 2012 to one of these same inventors. These patents describe improvements to the on-coil switched-mode amplifiers including the use of CMCD amplifiers, switched-mode pre-amplification, and amplitude modulation (AM) feedback for the on-coil switched-mode amplifiers. Once again, as these on-coil switched-mode amplifiers were built and used, further research revealed the need for further optimizations, particularly in telemetry systems.

BRIEF DESCRIPTION OF THE DRAWINGS

The accompanying drawings, which are incorporated in and constitute a part of the specification, illustrate various example systems, methods, and other embodiments of various aspects of the invention. It will be appreciated that the illustrated element boundaries (e.g., boxes, groups of boxes, or other shapes) in the figures represent one example of the boundaries. One of ordinary skill in the art will appreciate that in some embodiments one element may be designed as multiple elements, multiple elements may be designed as one element, an element shown as an internal component of another element may be implemented as an external component and vice versa, and so on. Furthermore, elements may not be drawn to scale.

DETAILED DESCRIPTION

Example apparatus, methods, and other embodiments acquire telemetry data from a portion of an MR apparatus (e.g., operating transmit coil, amplifier on transmit coil, component of amplifier on transmit coil) to facilitate understanding how an apparatus, coil, amplifier, or component is operating and, in one example, to facilitate dynamically adapting the operation of the apparatus, coil, amplifier, or component. Conventionally, the environment in which MR transmit coils operate, including strong magnetic fields, rapidly changing gradient fields, and complex pulse sequences, has made it difficult, if even possible, to acquire telemetry data from an operating apparatus, coil, amplifier, or smaller component.

In some MRI environments, multiple transmit coils may co-operate to produce a desired condition (e.g., flat field). The co-operation may include signal cancelling between coils. As coils become more complicated due, for example, to on-coil amplifiers (e.g., CMCD amplifier, switched-mode, current-source amplifier), it becomes more important to monitor the coil or amplifier performance. It is important to know whether a coil, amplifier, or amplifier component is operating correctly (e.g., within an envelope), under-performing, over-performing, or not performing at all, so that an undesired or even dangerous condition can be avoided. For example, if an amplifier has failed, a field may no longer be a flat field, which may influence specific absorption rate (SAR), heating, imaging, or other items. More generally, if a coil, amplifier, or component is not operating as desired, then a target field may not exhibit the properties desired and expected for that field.

Acquiring real-time telemetry data facilitates understanding how an apparatus, coil, amplifier, or component is operating, which in turn facilitates providing real-time control to the apparatus, coil, amplifier, or component. Conventionally, it may have been difficult, if even possible at all, to acquire this real-time telemetry data due, for example, to cabling issues. For example, running copper wires through a field produced by an MR apparatus may have produced both safety and antenna issues. The safety issues may have included, for example, heating of the copper wire due to the presence of changing electromagnetic fields. The antenna issues may have included, for example, having the copper wire transmit energy into a field or having the copper wire receive signals from the environment. Even if copper were a viable transmission media for real-time telemetry data, which it may not be, the price of copper may have been an issue.

Figure 1:
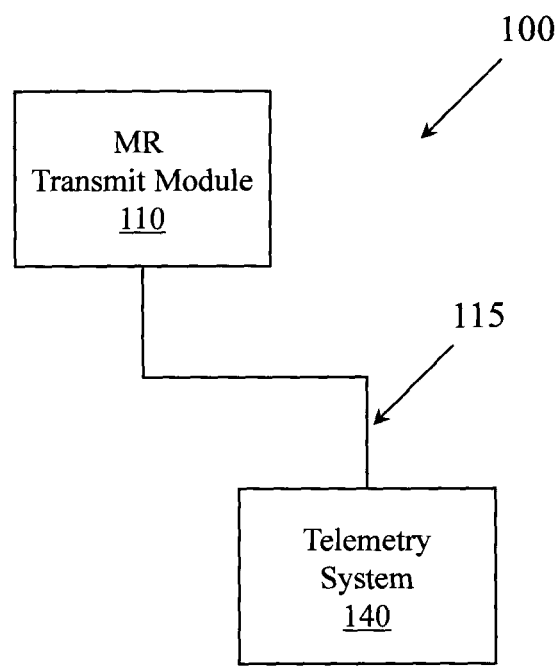
FIG. 1 illustrates a portion of an MR apparatus interacting with a fiber optic telemetry system.

FIG. 1 illustrates a portion 100 of an apparatus that includes an MR transmit module 110. The transmit module 110 may include, for example, a transmit coil, control circuitry, amplifiers, and other electronic components. The transmit module 110 may be connected to a telemetry system 140. The telemetry system 140 may acquire signals from the transmit module 110 via fiber optic cable 115. In one embodiment, the signals may be digital or analog. In one embodiment, the telemetry system 140 may report on the operation of the transmit module 110 or components of the transmit module 110. In another embodiment, the telemetry system 140 may analyze the operation of the transmit module 110 or components of the transmit module 110 to determine whether the transmit module 110 or components thereof are operating within a desired envelope or within a tolerance of a desired level. For example, it may be desirable for one component to produce a signal having power in the range of 1 W to 3000 W. Therefore, telemetry data about the wattage being produced may be provided from MR transmit module 110 to telemetry system 140 via fiber optic cable 115. In yet another embodiment, the telemetry system 140 may provide control signals back to the transmit module 110. The control signals may be computed as a function of the signals acquired from the transmit module 110 via fiber optics 115. The control signals may be coarsely grained (e.g., turn on, turn off) or may be more finely grained (e.g., increase power, decrease power). In one embodiment the control signals may be directed at a larger system (e.g., entire transmit module 110) while in another embodiment the control signals may be directed at a smaller system (e.g., an amplifier in transmit module 110, a coil in transmit module 110). For example, if the component that was supposed to produce a signal with a power between 1 W and 2 W is actually producing a signal with a power of 50 W, then a control signal may be generated to shut down the system before an undesired result (e.g., burnt out component) occurs.

Figure 2:
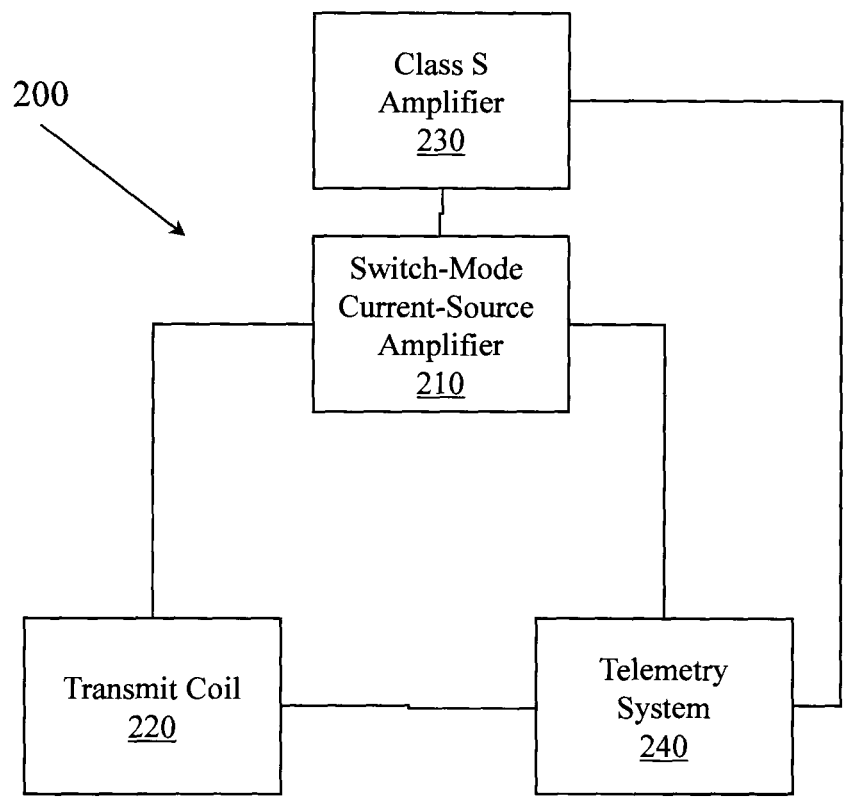
FIG. 2 illustrates a portion of an MR apparatus interacting with a fiber optic telemetry system.

FIG. 2 illustrates a portion 200 of an apparatus that includes an MR transmit coil 220 being driven by a switched-mode current-source amplifier 210. The switched-mode current-source amplifier 210 may receive a supply voltage from, for example, a class S amplifier 230. Signals from the class S amplifier, 230, various components of the class S amplifier 230, from the amplifier 210, or from various components of the amplifier 210 may be acquired and provided to a telemetry system 240. Additionally or alternatively, signals from the transmit coil 220 or from various components of the transmit coil 220 may be acquired and provided to the telemetry system 240. The signals may be transmitted to the telemetry system 240 via fiber optic cables. Unlike copper wires which may be problematic in an MR environment, fiber optic cables facilitate safely transmitting signals from the amplifiers 210 and 230 or coil 220 to the telemetry system 240.

In one embodiment, the switched-mode current-source amplifier 210 may be a current mode class D (CMCD) amplifier. Amplifier 210 may be a circuit whose components receive, process, or transmit analog or digital signals. Some of the analog signals may be considered to be "pseudo-digital" signals that are capable of being transmitted over fiber optic cable. Fiber optic cable may be well-suited to transmitting digital signals. However, fiber optic cable may not be as well-suited to transmitting analog signals. Thus, while it may appear attractive to place an analog-to-digital (ADC) converter on the coil 220, this may not be an appropriate approach. For example, electromagnetic interference, cost, complexity, and size issues may prevent the placement of an ADC on the coil 220. Therefore, example apparatus and methods may transmit digital, pseudo-digital, or analog signals over the fiber optic cable. Since the distance over which the signals are carried is short, and since the frequency of the analog signals may fall within a narrow range (e.g., 1-5 MHz) that is suitable for fiber optic cable, the fiber optic cable may provide adequate performance for even the analog signals. An ADC in the telemetry system 240 may digitize received analog signals for further processing. The distance from inside the bore to outside the Faraday cage in which the MRI apparatus is located may be, for example, ten meters or less. While it may be infeasible to run copper cables from inside the bore to outside the Faraday cage due to environmental issues (e.g., main magnetic field, varying magnetic field), it is feasible to run fiber optic cables through that same environment to carry telemetry data to the telemetry system 240.

Figure 3:
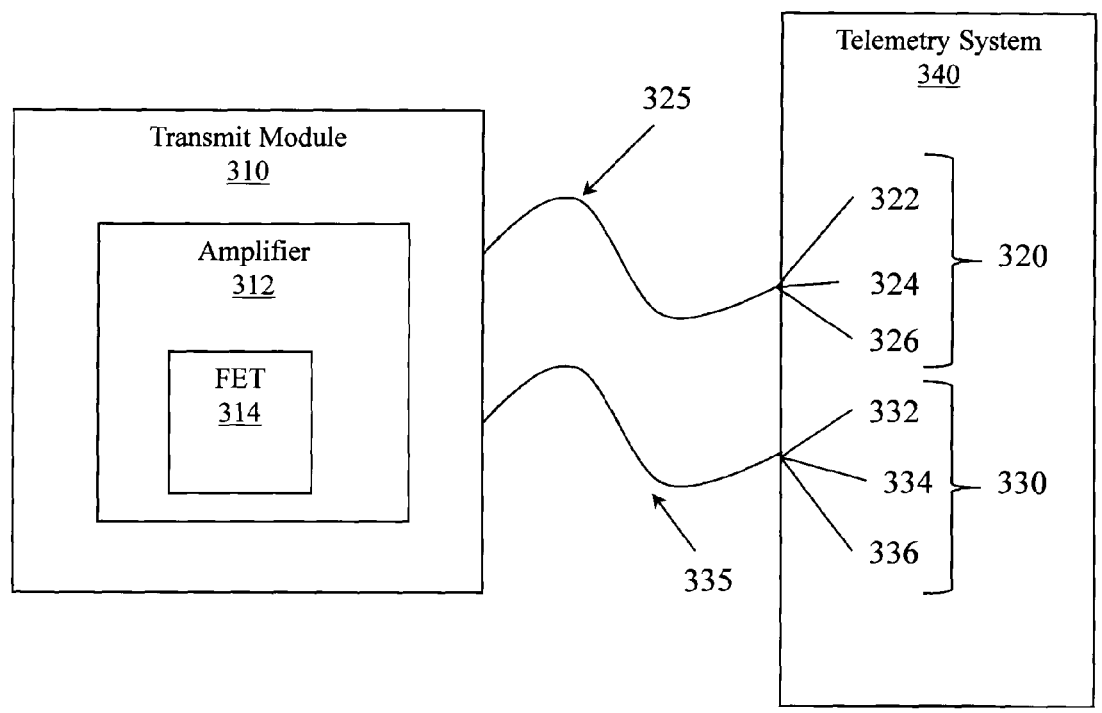
FIG. 3 illustrates example analog and digital signals handled by a fiber optic telemetry system.

FIG. 3 illustrates example digital signals 320 being provided to a telemetry system 340 via fiber optics 325. FIG. 3 also illustrates example analog signals 330 being provided to the telemetry system 340 via fiber optics 335. The digital signals 320 or the analog signals 330 may be acquired from a transmit module 310, from a component (e.g., amplifier 312) of the transmit module 310, from an element (e.g., FET 314) of the amplifier 312, or from other parts of an apparatus.

The digital signals 320 may include, for example, a slope comparator output 322, a module inhibit signal 334, or a pulse width modulation (PWM) signal 326. Additional and/or different digital signals may be acquired. The slope comparator output 322 may describe, for example, the raw output of a slope comparator found in a pulse width modulator associated with transmit module 310. The module inhibit signal 324 may be used to deactivate circuitry in the transmit module 310. The circuitry may be deactivated, for example, to facilitate reducing noise in received NMR signals. The module inhibit signal 324 may inhibit a final PWM signal when the set point of the amplifier 312 is below a threshold. The PWM signal 326 may be a PWM signal that is input into a class S modulator in transmit module 310. The PWM signal 326 may, for example, control the bias voltage of the amplifier 312. A member of the digital signals 320 may be able to be placed directly on a fiber optic cable or may be able to directly drive the fiber optic channels connecting the transmit module 310 and the telemetry system 340. Digital signals 330 may be acquired from detectors or traces on a circuit and placed on a fiber optic cable that connects transmit module 310 to telemetry system 340.

The analog signals 330 may include, for example, an envelope set point signal 332, an output envelope signal 334, or an error amplifier out signal 336. Additional and/or different signals may be acquired. In one embodiment, the analog signals 330 may have frequencies less than 2 MHz, which may make the analog signals 330 suitable for fiber optic transmission over the relevant distances (e.g., 5-20 meters). The envelope point signal 332 may represent the envelope (e.g., high current threshold, low current threshold) of the RF input waveform provided to control the transmit module 310. The envelope point signal 332 may be the set point for the transmit module 310 control loop. The output envelope signal 334 may be the measured envelope (e.g., maximum current detected, minimum current detected) of the transmit module 310 output current. In theory, the transmit module 310 control loop regulates the output current to be equal to the envelope set point, which was described by envelope set point signal 332. The error amplifier out signal 336 may be the output of the control loop error amplifier.

While the digital signals 320 may be able to directly drive the fiber optic channels connecting the transmit module 310 and the telemetry system 340, the analog signals 330 may not be able to perform a similar action. Therefore, to achieve desired linearity on the analog channels 335, example apparatus and methods may employ a modified sigma delta ($\Sigma\Delta$) modulation scheme. A conventional $\Sigma\Delta$ modulation may use a fixed sampling clock. One example $\Sigma\Delta$ modulator uses a variable frequency relaxation oscillator as a digital-to-analog converter (DAC).

Once the on-coil switched-mode amplifier for MRI transmit coils was invented, the need arose for pre-amplification (U.S. Pat. No. 8,294,465) and for the use of improved (e.g., current mode class D amplifiers) (U.S. Pat. No. 8,294,464). Once these refinements to on-coil switched-mode amplifiers for MRI transmit coils were available, work could proceed on further optimizing performance, design, cost, safety, and other factors. One improvement concerned understanding how various components in the on-coil switched-mode amplifiers were operating. Another improvement concerned dynamically reconfiguring individual components of the on-coil switched-mode amplifiers, reconfiguring the overall amplifier, or even reconfiguring the entire MR system based on data acquired through the fiber optic telemetry system.

Figure 4:
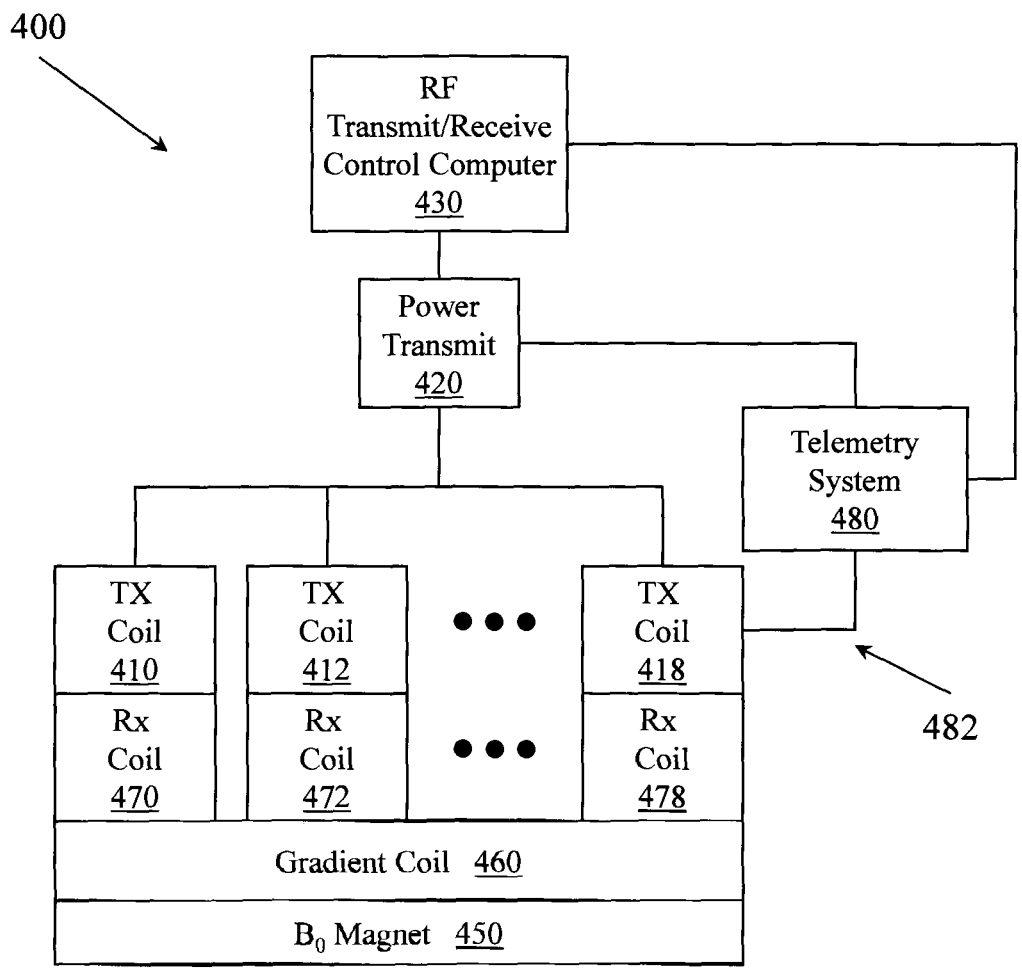
FIG. 4 illustrates a portion of an MR apparatus interacting with a fiber optic telemetry system.

FIG. 4 illustrates a portion of an example MR system 400 that uses multiple independent transmit coils (e.g., 410, 412 . . . 418) and multiple receive coils (e.g., 470, 472 . . . 478). The transmit coils may have on-coil switched-mode amplifiers (e.g., CMCD amplifier) that facilitate improved parallel transmission in MRI. In one example, an "on-coil" amplifier is an amplifier that performs within the bore of a magnet in an MRI apparatus. One skilled in the art will appreciate that MRI apparatus are generally enclosed in a bounding Faraday cage. In another example, an "on-coil" amplifier is an amplifier that performs outside the bore of the magnet yet still within the volume of space enclosed by a bounding Faraday cage. In yet another example, an "on-coil" amplifier is an amplifier that performs within a distance from the transmit coil of less than one wavelength of the RF signal produced by the transmit coil. As used herein, "on-coil" refers to the position of the amplifier. In different embodiments, the on-coil amplifier may be placed on a circuit board that includes the transmit coil, may be placed within one millimeter of the transmit coil, may be placed within one centimeter of the transmit coil, may be placed within one meter of the transmit coil, may be placed within two meters of the transmit coil, or may be placed at other locations.

The transmit coils may be powered by digital controllers (e.g., power transmitters 420) that are controlled by a computer 430. Thus, synchronization may be improved over conventional systems. Using a single digital controller 420 may also reduce issues associated with physical layout, synchronization, heating, and cooling. The electronic components (e.g., FETs) in the on-coil switched-mode amplifier facilitate controlling the coils with a digital signal. Thus, the transmit coils may receive a digital signal and produce an analog signal having improved characteristics.

Conventionally, the various components in FIG. 4 would have been assumed to be operating correctly. Only after an undesirable result (e.g., poor image, exceeding SAR threshold, heating) occurred would the assumption be challenged. Example telemetry systems 480 acquire signals that facilitate not only understanding how various components are operating, but also facilitate real-time control of components, systems, or entire MR apparatus.

Telemetry system 480 may acquire digital or analog telemetry signals from various components of system 400 and deliver control signals to various components of system 400. Telemetry system 480 is illustrated being connected by fiber optic cable 482 to transmit coil 418. Telemetry system 480 is also connected to power transmitter 420 and control computer 430. While a single connection to transmit coil 418 is illustrated, telemetry system 480 may also be connected to the other transmit coils (e.g., 410, 412, . . . 418) by fiber optic cable and may receive analog or digital telemetry signals from those coils. In different embodiments there may be multiple cables between a transmit coil and telemetry system 480. In one embodiment, telemetry system 480 may simply report on or display information about the telemetry signals. In another embodiment, telemetry system 480 may determine control signals as a function of the received telemetry signals and provide the control signals to, for example, RF transmit/receive control computer 430. In another embodiment, telemetry system 480 may send a control signal (e.g., turn off now) directly to a transmit coil, to an element (e.g., amplifier) on a transmit coil, to a component (e.g., oscillator) on an element, or to other apparatus.

In different embodiments or at different times, the telemetry channels that connect to the telemetry system 480 may be always active, always inhibited, or selectively (in)active. Whether a channel is (in)active may be a function, for example, of the set point of the input RF envelope. When the channels are configured to be selectively (in)active, fiber channels may be automatically disabled when the amplifier is idle (e.g., not driving a transmit coil during the time when NMR signals are expected to be received). This may reduce the likelihood that telemetry signals on a fiber optic channel might contaminate a received NMR signal and thereby damage the SNR of the received NMR signal.

Figure 5:
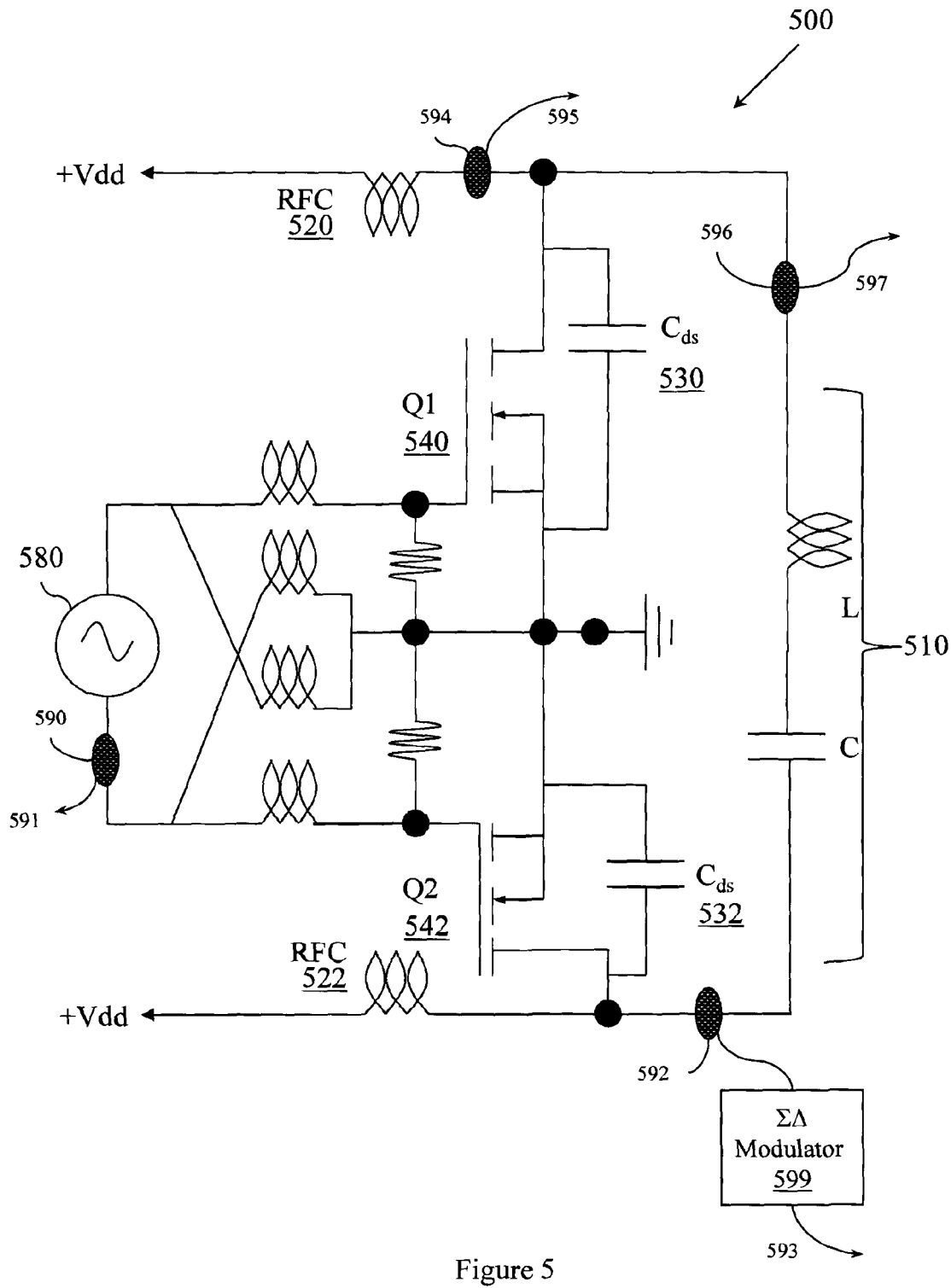
FIG. 5 illustrates a current-mode class-D amplifier topology for use in parallel MRI transmission involving on-coil switched-mode amplification.

FIG. 5 illustrates an example current-mode class-D amplifier topology 500 that includes telemetry signal detectors connected to fiber optic channels for delivering telemetry signals acquired by the detectors. For example, detector 596 is illustrated as residing on the LC leg of topology 500. Detector 596 may acquire telemetry data and provide that data through fiber optic channel 597. Similarly, detectors 590, 592, and 594 may acquire signals and provide them over fiber optic channels 591, 593, and 595 respectively. The signals may be digital signals that can be provided as-is to a fiber optic channel or may be analog signals that may be pre-processed using, for example, sigma-delta modulation, before being provided to a fiber optic channel. For example, the signal acquired by detector 592 may be an analog signal. Before placing the analog signal on fiber 593, the signal may be modulated using sigma delta modulator 599. Detectors 592, 594, and 596 may more generally be referred to as telemetry signal acquisition elements. The "detectors" may take forms including but not limited to multiplexers, voltage detectors, current detectors, frequency detectors, pulse time detectors, power detectors, or signal detectors. While detectors 592, 594, and 596 are illustrated as being built into topology 500, in another embodiment a separate circuit or separate circuit elements may function as telemetry signal acquisition elements.

Topology 500 may be referred to collectively as a CMCD amplifier. A coil configured with topology 500 may be referred to as an LC-switched-mode coil. In the illustration, the coil is represented by the series LC leg 510. The L refers to inductance in the coil 510 and the C refers to capacitance in the coil 510. The two chokes RFC (e.g., 520, 522) act as current-sources. The drain-source capacitances $C_{ds}$ (e.g., 530, 532) are in series with the coil 510. Alternative shunting of an applied DC voltage to ground as an FET is driven to saturation produces excitation at desired RF frequencies. In one example, element 580 corresponds to an RF transmission unit 1060 in FIG. 10. While LC Leg 510 is illustrated in one configuration in FIG. 5, it is to be appreciated that an LC leg may have different filter configurations and may include both parallel and serial components as well as combinations thereof.

The example CMCD design may be implemented on or near an array of surface coils of various sizes (e.g., 8.5 cm×8.5 cm). The coils may include various shielding configurations (e.g., 12.5 cm×12.5 cm). The coils may be tuned to different field frequencies (e.g., 63 MHz, 128 MHz, 300 MHz) corresponding to different main magnetic field strengths or different nuclei that can give an NMR signal. In one embodiment, the coils may be single turn or multi-turn coils. Note that the terminals of coil 510 are attached between the drains of the two FETs (Q1 540, Q2 542) and tuned so that the circuit is series resonant when one of the FETs is switched on. In one example, both FETs may be driven out of phase to optimize efficiency. While two FETs (Q1 540, Q2 542) are illustrated, it is to be appreciated that two or more FETs may be employed.

Figure 6:
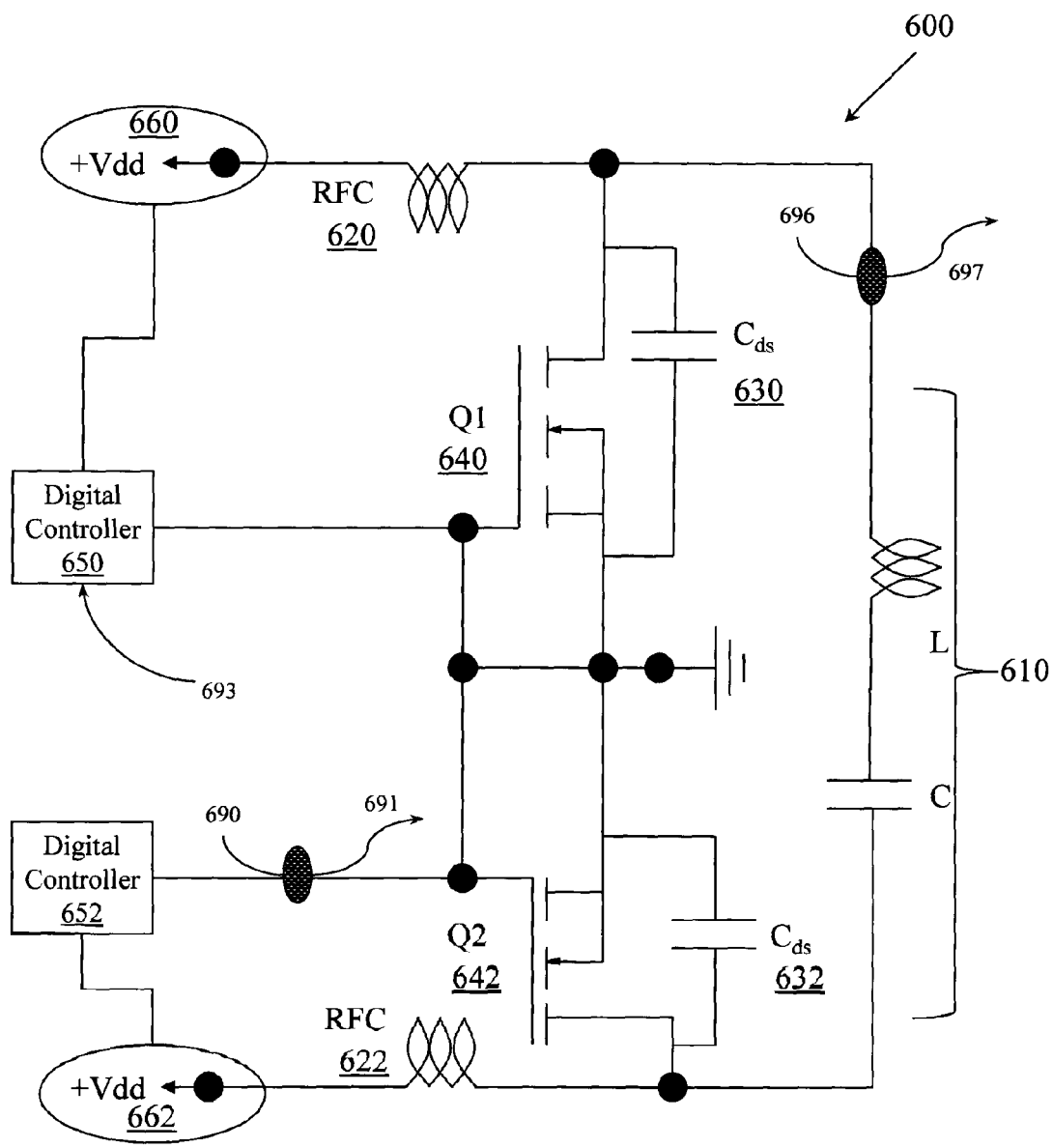
FIG. 6 illustrates a topology in which voltage and/or current-sources are additionally and/or alternatively digitally controllable.
Figure 7:
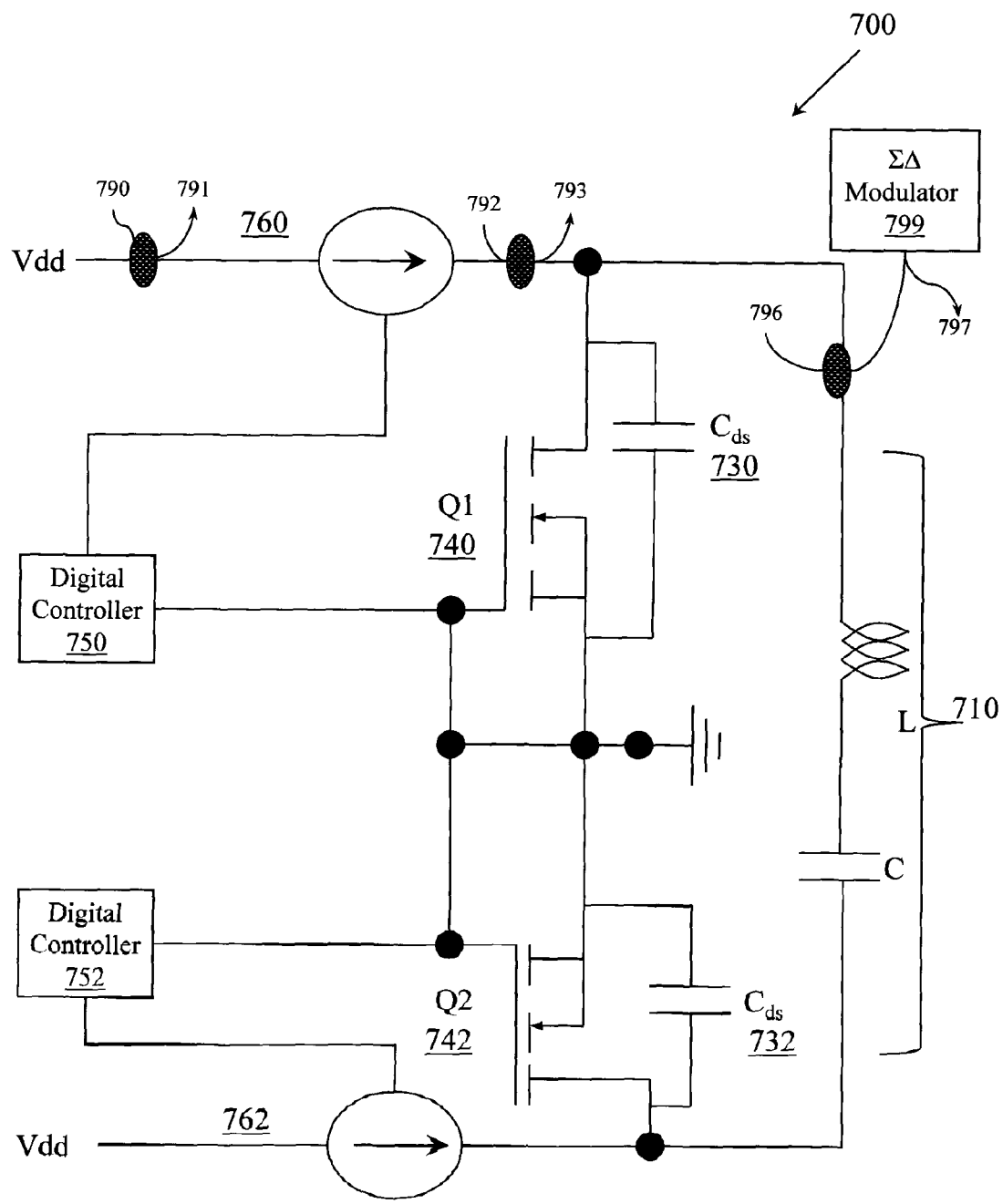
FIG. 7 illustrates a topology in which current-sources are additionally and/or alternatively digitally controllable.

It is to be appreciated that FIG. 5 is one example topology. FIGS. 6 and 7 illustrate different examples and illustrate the additional and/or alternative digital control of current-sources and/or supplies. These figures generally describe an "on-coil" CMCD amplifier. "On-coil" may mean on the coil, near the coil, or within a certain distance of the coil. Since the amplifier is located on the coil, frequency matching is not required. This facilitates performing a one-time load-independent match for the amplifier. When the amplifier is a class-D amplifier, a digital input can be employed. Example fiber optic telemetry systems may be employed with different types of amplifiers including on-coil amplifiers, CMCD amplifiers, switched-mode amplifiers, switched-mode current-source amplifiers, and other amplifiers and components.

FIG. 6 illustrates a topology 600 in which voltage and/or current-sources are additionally and/or alternatively digitally controllable. Topology 600 may be arranged, for example, as a circuit. FIG. 6 includes several elements similar to those described in connection with topology 500 (FIG. 5). For example, topology 600 includes an LC leg 610, two current-sources 620 and 622, two drain-source capacitances 630 and 632, and two FETs 640 and 642. In addition to the digital control in FIG. 5, FIG. 6 illustrates a digital controller 650 and a digital controller 652. These digital controllers provide digital control of the {+Vdd, RFC} elements 660 and 662. This digital control facilitates improving amplitude modulation accuracy and ease of use.

Topology 600 provides improvements over conventional topologies by including telemetry signal detectors that are connected to fiber optical channels for delivering telemetry signals acquired by the detectors. For example, detector 696 is illustrated as residing on the LC leg of topology 600. Detector 696 may acquire telemetry data and provide that data through fiber optic channel 697. Similarly, detector 690 may acquire signals and provide them over fiber optical channel 691. The signals may be digital signals that can be provided as-is to a fiber optical channel or may be analog signals that may be pre-processed using, for example, sigma-delta modulation, before being provided to a fiber optic channel. While detectors 690 and 696 are illustrated, more generally, topology 600 may interact with a telemetry apparatus that includes a telemetry signal acquisition element and a fiber optic cable. The fiber optic cable may carry an output signal through a field produced by an MR apparatus in which topology 600 resides. The output signal may be produced from the telemetry signal by a telemetry signal output element.

More generally, FIG. 6 illustrates an apparatus having at least two FETs (e.g., 640, 642) connected by a coil 610 including an LC leg and having at least one telemetry signal detector 690 that provides at least one telemetry signal via fiber optic channel 691. The apparatus includes a controller (e.g., 650, 652) to input a digital signal to the at least two FETs (e.g., 640, 642) and to control the production of an output analog radio frequency (RF) signal, based, at least in part, on the digital signal. In one embodiment, a controller (e.g., digital controller 650) may receive an input on a fiber optic channel 693. The input received on fiber optic channel 693 may be designed to control topology 600 or to control just a portion of topology 600. The input received on fiber optical channel 693 may have been computed as a function of telemetry signals provided from detectors 690 and 696 via fiber optic channels 691 and 697. The LC leg 610 selectively alters the output analog RF signal. The output analog RF signal is associated with parallel MRI transmission. The apparatus also includes at least two drain-source capacitances (e.g., 630, 632) in series with the coil 610. In one example, the digital control signal provided by digital controller 650 and/or 652 may be determinable from the desired analog RF signal by sigma delta modulation, pulse width modulation, pulse train optimization, and so on. In one example, the digital control signal may be a voltage in the range of 0.1V to 50V and the output analog RF signal may have a power in the range of 1 W to 3000 W.

In one example, the digital controllers 650 and 652 are connected to the at least two FETs (e.g., 640, 642) by a dedicated connection. The dedicated connection may be, for example, a wireless connection, a fiber optic connection, or other connection. While FIG. 6 illustrates a single apparatus 600, it is to be appreciated that multiple instances of the apparatus 600 may be implemented on an array of surface coils. These surface coils may be tuned to different field strengths and may include a shielding element.

FIG. 7 illustrates a topology 700 in which current-sources are additionally and/or alternatively digitally controllable. Topology 700 may be arranged, for example, as a circuit. FIG. 7 includes several elements similar to those described in connection with topology 600 (FIG. 6). For example, topology 700 includes an LC leg 710, two current-sources 760 and 762, two drain-source capacitances 730 and 732, two FETs 740 and 742, and two digital controllers 750 and 752. Note that the {+Vdd, RFC} elements 660 and 662 (FIG. 6) have been replaced with more generic current-sources 760 and 762, which are digitally controlled by digital controllers 750 and 752 respectively. Once again this digital control facilitates improving amplitude modulation accuracy and ease of use.

FIG. 7 also includes detectors 790, 792, and 796 that detect telemetry data and provide that telemetry data over fiber optic channels 791, 793, and 797 respectively. Telemetry data from detector 796 may be modulated by modulator 799 before being placed on channel 797.

Figure 8:
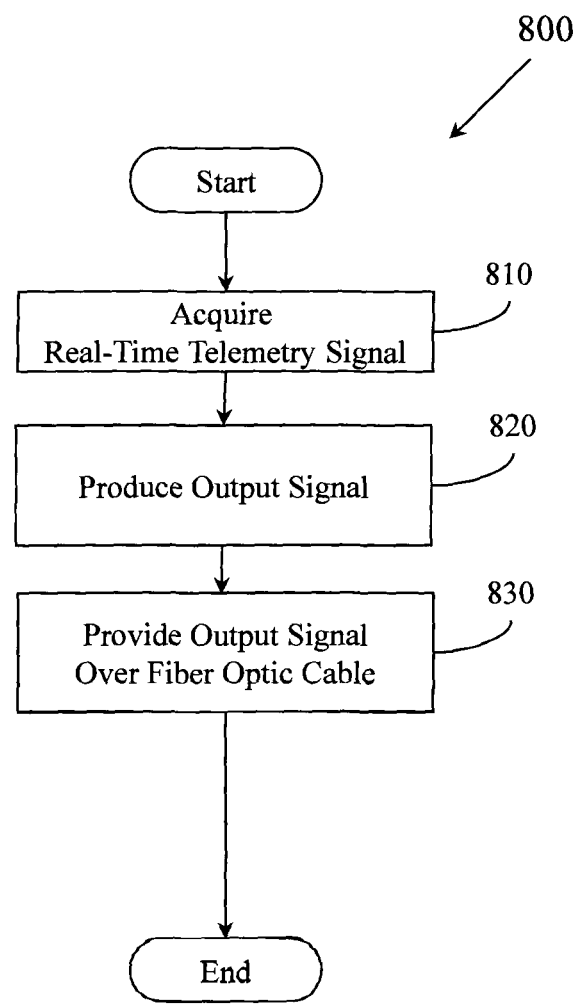
FIG. 8 illustrates a method associated with a fiber optic telemetry system.

FIG. 8 illustrates a method 800 associated with a fiber optic telemetry system. Method 800 includes, at 810, acquiring, in real-time, a telemetry signal from a transmit coil in a magnetic resonance imaging (MRI) apparatus. The telemetry signal may be a digital signal (e.g., pulse width modulation signal), an analog signal (e.g., envelope set point signal), or a pseudo-digital signal.

Method 800 may also include, at 820, producing an output signal. Upon determining that the telemetry signal is a digital signal, producing the output signal may include producing an output digital signal representing the telemetry signal. Upon determining that the telemetry signal is an analog signal, producing the output signal may include producing a modulated analog signal from the analog signal using sigma-delta modulation.

Method 800 may also include, at 830, providing the output signal on the fiber optic cable. The output signal may be provided, for example, to a reporting logic, to an analysis logic, to a control signal logic, or to other destinations.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and other entities. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

Figure 9:
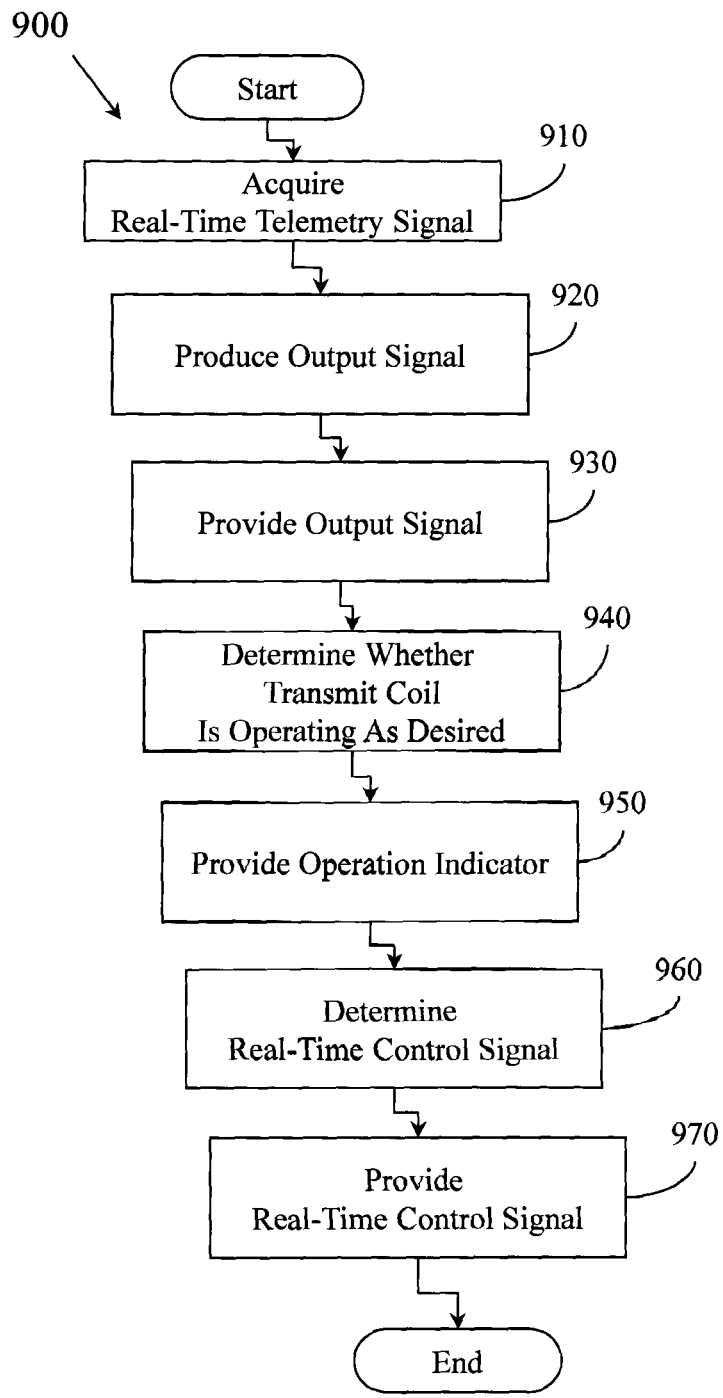
FIG. 9 illustrates a method associated with a fiber optic telemetry system.

FIG. 9 illustrates a method 900 associated with a fiber optic telemetry system. Method 900 includes some actions similar to those described in connection with method 800 (FIG. 8). For example, method 900 includes acquiring a real-time telemetry signal at 910, producing an output signal at 920, and providing the output signal at 930. However, method 900 also includes additional actions.

For example, method 900 includes, at 940, determining whether the transmit coil is operating as desired based, at least in part, on the telemetry signal. For example, the telemetry signal may indicate that the transmit coil or a portion thereof is operating inside desired operating parameters or outside desired operating parameters. In one example, the telemetry signal may indicate that the transmit coil or portion thereof is not even operating at all.

Method 900 also includes, at 950, providing an indication of whether the transmit coil is operating as desired. The indication may take various forms including, but not limited to, a voltage, an interrupt signal in a computer system, a waveform, a display, or a sound.

Method 900 may also include, at 960, determining a real-time control signal from the telemetry signal. For example, if the telemetry signal indicates that a transmit coil or component thereof is running at too high a voltage then the real-time control signal may be a decrease voltage signal.

Method 900 also includes, at 970, selectively providing the real-time control signal to the MRI apparatus. In one embodiment, the real-time control signal is configured to alter the operation of an element of the transmit coil that produced the telemetry signal. In different embodiments, the real-time control signal may operate to increase or decrease a voltage, to increase or decrease a current, to increase or decrease a power, to increase or decrease a frequency, or to increase or decrease a pulse time.

Conventionally, the acts of acquiring telemetry signals, producing output signals, and providing output signals may have some effect on the MR environment. For example, interference may be introduced into a received NMR signal. Therefore, in one embodiment, method 900 may include selectively controlling the acquiring of the telemetry signal and the delivery of the output signal on the fiber optic cable. In one embodiment, the selective control may be exercised as a function of a set point of a radio frequency (RF) input envelope associated with the transmit coil. The set point may indicate whether the transmit coil is transmitting or is passive.

Figure 10:
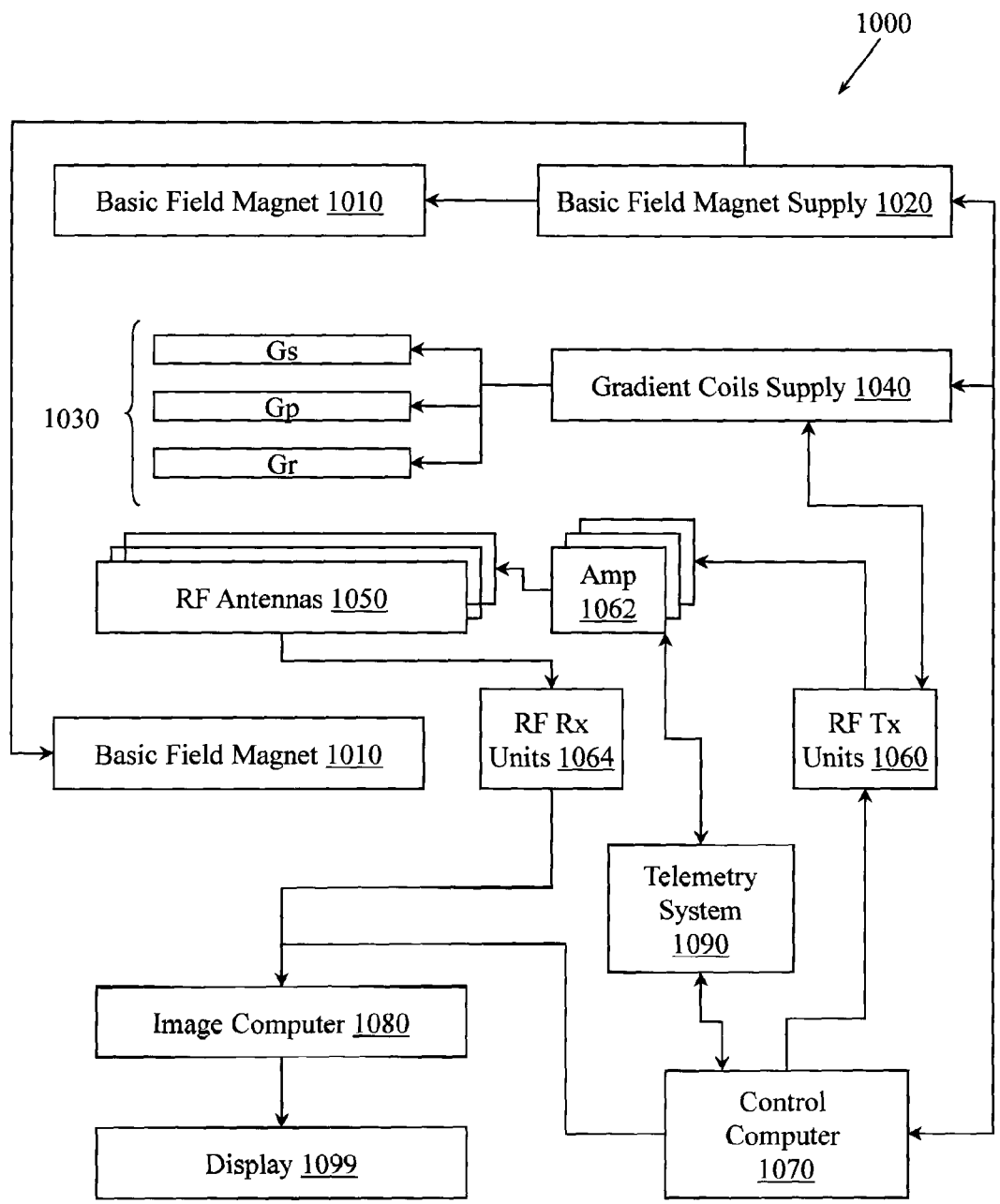
FIG. 10 illustrates an MRI apparatus configured to operate with a fiber optic telemetry system.

FIG. 10 illustrates an example MRI apparatus 1000 configured with a set of on-coil amplifiers 1062 to facilitate improved parallel transmission of analog RF signals used in MRI. In one embodiment, the on-coil amplifiers 1062 may be on-coil switched-mode (e.g., CMCD) amplifiers configured like those illustrated in FIGS. 5 through 7. In different embodiments, different amplifiers arranged in different configurations are possible. Consider a relationship between elements in FIG. 5 and elements in FIG. 10. The RF antennas 1050 may correspond in part to element 510 (FIG. 5). The amplifiers 1062 may correspond in part to topology 500, minus elements 510 and 580. The RF transmission (TX) units 1060 may correspond to element 580. Similar correlations may be made between elements in FIGS. 6 and 7.

The apparatus 1000 includes a basic field magnet(s) 1010 and a basic field magnet supply 1020. Ideally, the basic field magnets 1010 would produce a uniform $B_0$ field. However, in practice, the $B_0$ field may not be uniform, and may vary over an object being imaged by the MRI apparatus 1000. MRI apparatus 1000 may include gradient coils 1030 configured to emit gradient magnetic fields like $G_S$, $G_P$ and $G_R$. The gradient coils 1030 may be controlled, at least in part, by a gradient coils supply 1040. In some examples, the timing, strength, and orientation of the gradient magnetic fields may be controlled, and thus selectively adapted, during an MRI procedure.

MRI apparatus 1000 may include a set of RF antennas 1050 that are configured to generate RF pulses and to receive resulting MR signals from an object to which the RF pulses are directed. In one example, the RF antennas 1050 may be considered to correspond, at least in part, to element 510 (FIG. 5). In some examples, how the pulses are generated and how the resulting MR signals are received may be controlled, and thus may be selectively adapted, during an MRI procedure. Separate RF transmission and reception-coils can be employed. The RF antennas 1050 may be controlled, at least in part, by a set of RF transmission units 1060. An RF transmission unit 1060 may provide a signal to an amplifier 1062, which may manipulate the signal and provide a different signal to an RF antenna 1050. In one embodiment, the amplifier 1062 may be a switched-mode current-source amplifier having gallium nitride FETs. The signal may be manipulated (e.g., amplified) using circuits described in connection with FIGS. 5-7, or in other ways.

The gradient coils supply 1040 and the RF transmission units 1060 may be controlled, at least in part, by a control computer 1070. In one example, the control computer 1070 may be programmed to perform methods like those described herein. The MR signals received from the RF antennas 1050 can be employed to generate an image, and thus may be subject to a transformation process like a two dimensional FFT that generates pixilated image data. The transformation can be performed by an image computer 1080 or other similar processing device. The image data may then be shown on a display 1099. While FIG. 10 illustrates an example MRI apparatus 1000 that includes various components connected in various ways, it is to be appreciated that other MRI apparatus, NMR apparatus, or MR apparatus may include other components connected in other ways.

In one example, MRI apparatus 1000 may include control computer 1070 and a digital controller operably connected to the amplifiers 1062. The amplifiers 1062 may include a set of LC-switched-mode coils operably connected to the digital controller. In one example, a member of the set of LC-switched-mode coils may be individually controllable by the control computer 1070. Additionally, the control computer 1070 may provide an LC-switched-mode coil with a digital control signal and the LC-switched-mode coil may output an analog RF signal based, at least in part, on the digital control signal.

In one example, the set of LC-switched-mode coils may be operably connected to the control computer 1070 by dedicated connections. The dedicated connections may include a copper cable, a fiber optic cable, a wireless connection, or other connections. In one example, an LC-switched-mode coil may be operably connected to a local memory that stores bit patterns that control production of the analog RF signal. Thus, the digital control signal may identify a stored bit pattern.

In one example, MRI apparatus 1000 may include or be configured to interact with a fiber optic telemetry system 1090. Telemetry system 1090 may receive telemetry signals from, for example, amplifiers 1062. The signals may be analog signals or digital signals. The signals may concern the operation of an amplifier 1062 or of a component of the amplifier 1062. The amplifier 1062 may be connected to the telemetry system 1090 by fiber optic cable that is not negatively influenced beyond a tolerable threshold by the environment created by apparatus 1000. While telemetry system 1090 is illustrated being connected to amplifier 1062 by fiber optic cable, the telemetry system 1090 may, more generally, acquire telemetry data from components of apparatus 1000 via fiber optic cables. In one embodiment, the telemetry system 1090 may provide information or control signals to control computer 1070 which may in turn selectively control elements of apparatus 1000 as a function of the information or control signals.

Figure 11:
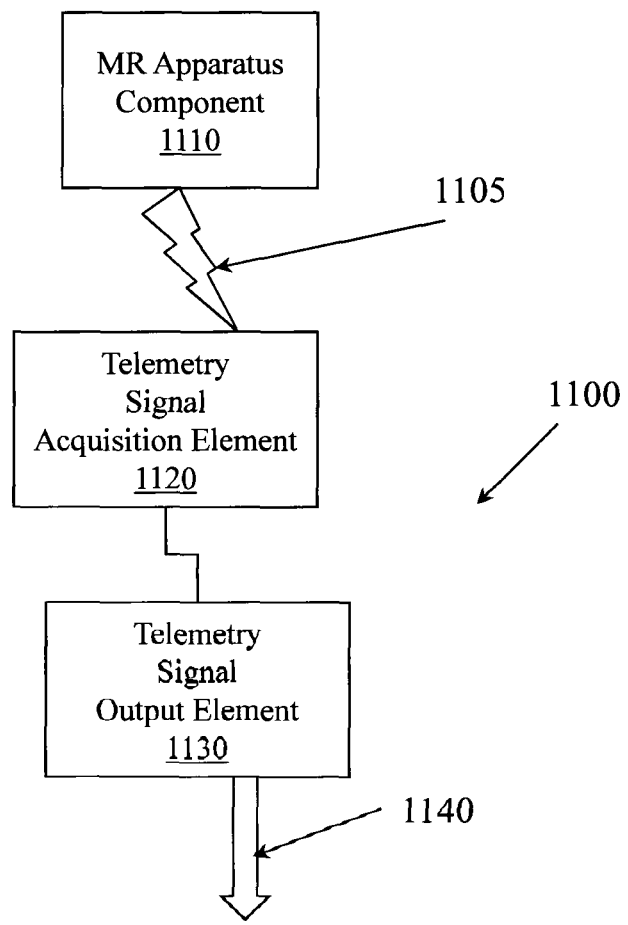
FIG. 11 illustrates an example telemetry apparatus for use with an MRI apparatus.

FIG. 11 illustrates a portion of an example telemetry apparatus for use with an MRI apparatus. Telemetry apparatus 1100 includes a telemetry signal acquisition element 1120 that acquires, in real-time, a telemetry signal 1105 from a component 1110 of an MR apparatus. The telemetry signal acquisition element 1120 may be incorporated into the component 1110, may be temporarily associated with the component 1110, may receive signals generated by component 1110, or may receive the telemetry signal 1105 in different ways.

Telemetry apparatus 1100 includes a telemetry signal output element 1130 that produces an output signal from the telemetry signal 1105. The output signal is placed on fiber optic cable 1140. The telemetry signal output element 1130 may be configured to produce a digital output signal from a digital telemetry signal, to place the digital telemetry signal on the cable 1140, to produce a modulated analog signal from an analog telemetry signal, to place an analog signal or modulated analog signal onto cable 1140, or to take other actions.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

To the extent that the term "includes" or "including" is employed in the detailed description or the claims, it is intended to be inclusive in a manner similar to the term "comprising" as that term is interpreted when employed as a transitional word in a claim.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

Although the subject matter has been described in language specific to structural features or methodological acts, it is to be understood that the subject matter defined in the appended claims is not necessarily limited to the specific features or acts described above. Rather, the specific features and acts described above are disclosed as example forms of implementing the claims.

What is claimed is:

1. A telemetry apparatus for use with a magnetic resonance (MR) apparatus, comprising:
a telemetry signal acquisition element configured to acquire a telemetry signal from a component in the MR apparatus;
a fiber optic cable configured to carry an output signal through a field produced by the MR apparatus;
a telemetry signal output element configured to produce the output signal from the telemetry signal and to transmit the output signal via the fiber optic cable;
a control logic configured to produce a control signal as a function of the output signal and to provide the control signal to the MR apparatus; and the control signal being an on/off signal, an increase voltage signal, a decrease voltage signal, an increase current signal, a decrease current signal, an increase power signal, a decrease power signal, an increase frequency signal, a decrease frequency signal, an increase pulse time signal, or a decrease pulse time signal.

2. The telemetry apparatus of claim 1, the component in the MR apparatus being a transmit coil.

3. The telemetry apparatus of claim 1, the telemetry signal acquisition element being a multiplexer.

4. The telemetry apparatus of claim 1, the telemetry signal acquisition element being a voltage detector, a current detector, a power detector, a frequency detector, or a pulse time detector.

5. The telemetry apparatus of claim 1, the MR apparatus being a magnetic resonance imaging (MRI) apparatus or a magnetic resonance spectroscopy (MRS) apparatus.

6. The telemetry apparatus of claim 1, the telemetry signal being a digital signal.

7. The telemetry apparatus of claim 6, the digital signal being a slope comparator output, a module inhibit signal, or a pulse width modulation signal.

8. The telemetry apparatus of claim 6, the telemetry signal output element being configured to produce the output signal from the digital signal without modulating the telemetry signal.

9. The telemetry apparatus of claim 1, the telemetry signal output element being configured to transmit two or more output signals via the fiber optic cable.

10. A telemetry for use with a magnetic resonance (MR) apparatus, comprising:
a telemetry signal acquisition element configured to acquire a telemetry signal from a component in the MR apparatus;
a fiber optic cable configured to carry an output signal through a field produced by the MR apparatus;
telemetry signal output element configured to produce the output signal from the telemetry signal and to transmit the output signal via the fiber optic cable; and
the component in the MR apparatus being a transmit coil configured with an on-coil amplifier;
the on-coil amplifier being a switched mode amplifier, a switched-mode current-source amplifier, or a current-mode class-D (CMCD) amplifier.

11. A telemetry apparatus for use with a magnetic resonance (MR) apparatus, comprising:
a telemetry signal acquisition element configured to acquire a telemetry signal from a component in the MR apparatus;
a fiber optic cable configured to carry an output signal through a field produced by the MR apparatus;
a telemetry signal output element configured to produce the output signal from the telemetry signal and to transmit the output signal via the fiber optic cable;
a control logic configured to produce a control signal as a function on the output signal and to provide the control signal to the MR apparatus; and
the control signal being a pulse width modulation signal, a sigma delta modulation signal, or a pulse train optimization signal.

12. A telemetry apparatus for use with a magnetic resonance (MR) apparatus, comprising:
a telemetry signal acquisition element configured to acquire a telemetry signal from a component in the MR apparatus;
a fiber optic cable configured to carry an output signal through a field produced by the MR apparatus;
a telemetry signal output element configured to produce the output signal from the telemetry signal to transmit the output signal via the fiber optic cable; and
the output signal being an analog signal.

13. The telemetry apparatus of claim 12, the analog signal being an envelope set point signal, an output envelope signal, or an error amplifier output signal.

14. The telemetry apparatus of claim 12, the analog signal having a frequency of less than 2 MHz.

15. The telemetry apparatus of claim 12, the telemetry signal output element being configured with a sigma-delta modulator configured to produce a modulated analog signal from the analog signal by performing sigma-delta modulation on the analog signal,
the telemetry signal output element being configured to produce the output signal from the modulated analog signal.

16. The telemetry apparatus of claim 15, the sigma-delta modulator being configured with a variable frequency relaxation oscillator configured as a digital-to-analog converter.

17. A method, comprising:
acquiring, in real-time, a telemetry signal from a transmit coil in a magnetic resonance imaging (MRI) apparatus;
upon determining that the telemetry signal is a digital signal, producing an output digital signal representing the telemetry signal and placing the output digital signal on a fiber optic cable connected to the transmit coil; and
upon determining that the telemetry signal is an analog signal, producing a modulated analog signal from the analog signal using sigma-delta modulation, and placing the modulated analog signal on the fiber optic cable.

18. The method of claim 17, comprising providing an indication of whether the transmit coil is operating as desired based, at least in part, on the telemetry signal.

19. The method of claim 18, comprising determining a real-time control signal from the output digital signal or the modulated analog signal and selectively providing the real-time control signal to the MRI apparatus.

20. The method of claim 19, where the real-time control signal is configured to alter the operation of an element of the transmit coil that produced the telemetry signal.

21. The method of claim 20, comprising selectively controlling whether the telemetry signal is acquired and selectively controlling whether the output signal or the modulated analog signal are placed on the fiber optic cable as a function of a set point of a radio frequency (RF) input envelope associated with the transmit coil.

22. An MRI apparatus, comprising:
a digital controller;
a set of LC-switched-mode transmit coils operably connected to the digital controller, where a member of the set of LC switched-mode coils includes a field effect transistor based switched-mode current-source amplifier and a transmit coil that are controlled, at least in part, by a signal from the digital controller; and
a telemetry circuit configured to acquire a telemetry signal from the member of the set of LC-switched-mode coils and to provide the telemetry signal, via a fiber optic cable, to a region located outside a Faraday cage bounding the MRI apparatus.

* * * * *

UNITED STATES PATENT AND TRADEMARK OFFICE
CERTIFICATE OF CORRECTION

PATENT NO. : 9,536,423 B2  
APPLICATION NO. : 14/053305  
DATED : January 3, 2017  
INVENTOR(S) : Mark Griswold and Michael Twieg Page 1 of 1

It is certified that error appears in the above-identified patent and that said Letters Patent is hereby corrected as shown below:

Column 13, Line 31 - "telemetry for" should be -- telemetry apparatus for --

Signed and Sealed this  
Twenty-seventh Day of March, 2018

Andrei Iancu  
*Director of the United States Patent and Trademark Office*